US00PP28355P3

(12) United States Plant Patent
Hofmann

(10) Patent No.: US PP28,355 P3
(45) Date of Patent: Aug. 29, 2017

(54) ***NEMESIA* PLANT NAMED 'INNEMBLORA'**

(50) Latin Name: ***Nemesia strumosa*×*Nemesia fruticans***
Varietal Denomination: Innemblora

(71) Applicant: Silvia Hofmann, Mainz (DE)

(72) Inventor: Silvia Hofmann, Mainz (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 149 days.

(21) Appl. No.: 14/756,183

(22) Filed: Aug. 12, 2015

(65) Prior Publication Data

US 2017/0049034 P1 Feb. 16, 2017

(51) Int. Cl.
*A01H 5/02* (2006.01)

(52) U.S. Cl.
USPC ..... Plt./458

(58) Field of Classification Search
USPC ..... Plt./263.1, 458
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Nemesia* plant named 'Innemblora', characterized by its upright to somewhat outwardly spreading and mounding plant habit; vigorous growth habit; freely branching habit; freely flowering habit; long flowering period; dark orange-colored flowers that are sterile; and good summer garden performance.

1 Drawing Sheet

Botanical designation: *Nemesia strumosa*×*Nemesia fruticans*.

Cultivar denomination: 'INNEMBLORA'.

BACKGROUND OF THE INVENTION

The present invention relates to a new and distinct cultivar of *Nemesia* plant, botanically known as *Nemesia strumosa*× *Nemesia fruticans* and hereinafter referred to by the name 'Innemblora'.

The new *Nemesia* plant is a product of a planned breeding program conducted by the Inventor in Heidesheim and Gensingen, Germany. The objective of the breeding program is to create new semi-upright and freely branching *Nemesia* plants with good summer garden performance.

The new *Nemesia* plant originated from a cross-pollination made by the Inventor in August, 2011 in Heidesheim, Germany of a proprietary selection of *Nemesia strumosa* identified as code number N 05 82-1, not patented, as the female, or seed, parent with a proprietary selection of *Nemesia fruticans* identified as code number N 04 46-48, not patented, as the male, or pollen, parent. The new *Nemesia* plant was discovered and selected by the Inventor as a single flowering plant from within the progeny of the stated cross-pollination in a controlled environment in Heidesheim, Germany in April, 2012.

Asexual reproduction of the new *Nemesia* plant by terminal vegetative cuttings in a controlled environment in Gensingen, Germany since September, 2012, has shown that the unique features of this new *Nemesia* plant are stable and reproduced true to type in successive generations.

SUMMARY OF THE INVENTION

Plants of the new *Nemesia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Innemblora'. These characteristics in combination distinguish 'Innemblora' as a new and distinct *Nemesia* plant:

1. Upright to somewhat outwardly spreading and mounding plant habit.
2. Vigorous growth habit.
3. Freely branching habit.
4. Freely flowering habit.
5. Long flowering period.
6. Dark orange-colored flowers that are sterile.
7. Good summer garden performance.

Plants of the new *Nemesia* differ from plants of the female parent selection primarily in the following characteristics:

1. Plants of the new *Nemesia* and the female parent selection differ in flower color as plants of the female parent selection have white-colored flowers.
2. Flowers of plants of the new *Nemesia* are sterile whereas flowers of plants of the female parent selection are fertile.

Plants of the new *Nemesia* differ from plants of the male parent selection primarily in the following characteristics:

1. Plants of the new *Nemesia* are more upright than and not as trailing as plants of the male parent selection.
2. Flowers of plants of the new *Nemesia* are sterile whereas flowers of plants of the male parent selection are fertile.

Plants of the new *Nemesia* can be compared to plants of *Nemesia hybrida* 'Intrairedtwo', disclosed in U.S. Plant Pat. No. 23,061. In side-by-side comparisons conducted in Gensingen, Germany, plants of the new *Nemesia* differed from plants of 'Intrairedtwo' in the following characteristics:

1. Plants of the new *Nemesia* were more compact than plants of 'Intrairedtwo'.

2. Plants of the new *Nemesia* were more freely branching and denser than plants of 'Intrairedtwo'.
3. Plants of the new *Nemesia* and 'Intrairedtwo' differed in flower color as plants of 'Intrairedtwo' have dark red-colored flowers.

Plants of the new *Nemesia* can be compared to plants of *Nemesia hybrida* 'Intraigoldtwo', disclosed in U.S. Plant Pat. No. 23,062. In side-by-side comparisons conducted in Gensingen, Germany, plants of the new *Nemesia* differed from plants of 'Intraigoldtwo' in the following characteristics:

1. Plants of the new *Nemesia* were more compact than plants of 'Intraigoldtwo'.
2. Plants of the new *Nemesia* and 'Intraigoldtwo' differed in flower color as plants of 'Intraigoldtwo' have golden yellow-colored flowers.

BRIEF DESCRIPTION OF THE PHOTOGRAPHS

The accompanying colored photographs illustrate the overall appearance of the new *Nemesia* plant showing the colors as true as it is reasonably possible to obtain in colored reproductions of this type. Colors in the photographs may differ slightly from the color values cited in the detailed botanical description which accurately describe the colors of the new *Nemesia* plant.

The photograph on the right side of the sheet comprises a side perspective view of a typical flowering plant of 'Innemblora' grown in a container.

The photograph on the left side of the sheet is a close-up view of a typical flowering plant of 'Innemblora'.

DETAILED BOTANICAL DESCRIPTION

Plants used for the aforementioned photographs and following description were grown under conditions which closely approximate commercial production conditions during the summer in 11.5-cm containers in an outdoor nursery in Bonsall, Calif. During the production of the plants, day temperatures averaged 24° C., night temperatures averaged 10° C. and light levels ranged from 7,000 to 10,000 foot-candles. Plants were pinched two times and were nine weeks old when the photographs and description were taken. In the following description, color references are made to The Royal Horticultural Society Colour Chart, 2007 Edition, except where general terms of ordinary dictionary significance are used.

Botanical classification: *Nemesia strumosa*×*Nemesia fruticans* 'Innemblora'.

Parentage:

*Female, or seed, parent.*—Proprietary selection of *Nemesia strumosa* identified as code number N 05 82-1, not patented.

*Male, or pollen, parent.*—Proprietary selection of *Nemesia fruticans* identified as code number N 04 46-48, not patented.

Propagation:

*Type.*—By terminal vegetative cuttings.

*Time to initiate roots, summer.*—About 10 days at temperatures about 20° C.

*Time to initiate roots, winter.*—About 14 days at temperatures about 20° C.

*Time to produce a rooted young plant, summer.*—About 14 days at temperatures about 20° C.

*Time to produce a rooted young plant, winter.*—About 14 to 20 days at temperatures about 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous annual; upright to somewhat outwardly spreading and mounding plant habit; vigorous growth habit; freely branching habit; about 14 to 16 primary branches develop per plant each with multiple secondary laterals.

*Plant height.*—About 19.5 cm.

*Plant diameter.*—About 23 cm.

Lateral branch description:

*Length.*—About 20 cm.

*Diameter.*—About 3.5 mm.

*Internode length.*—About 3.7 cm.

*Strength.*—Strong.

*Aspect.*—Mostly upright to somewhat outwardly and curving upright.

*Texture.*—Smooth, glabrous.

*Color.*—Close to 146A.

Leaf description:

*Arrangement.*—Opposite, simple; sessile.

*Length.*—About 5.8 cm.

*Width.*—About 1.8 cm.

*Shape.*—Lanceolate.

*Apex.*—Acute.

*Base.*—Truncate; clasping.

*Margin.*—Sparsely dentate.

*Texture, upper and lower surfaces.*—Smooth, glabrous.

*Venation pattern.*—Pinnate; arcuate.

*Color.*—Developing leaves, upper surface: Close to N137C. Developing leaves, lower surface: Close to 137B. Fully expanded leaves, upper surface: Close to N137A; venation, close to 137B. Fully expanded leaves, lower surface: Close to 137B; venation, close to 137B.

Flower description:

*Flower arrangement and habit.*—Bilabiate single flowers arranged in terminal racemes; flowers develop acropetally towards the apex; flowers face upright to outwardly; freely flowering habit with about 28 flowers per inflorescence and more than 1,200 flowers per plant developing during the flowering season.

*Fragrance.*—None detected.

*Natural flowering season.*—Long flowering period, in Southern California, plants flower from mid-March to November; flowering continuous during this period.

*Flower longevity.*—Flowers last about three to four days on the plant; flowers not persistent.

*Inflorescence height.*—About 7.2 cm.

*Inflorescence diameter.*—About 3.4 cm.

*Flower diameter.*—About 1.8 cm.

*Flower depth.*—About 1.4 cm.

*Flower buds.*—Length: About 1.2 cm. Diameter: About 6 mm. Shape: Oval with a short spur. Color: Close to 187C to 187D.

*Petals.*—Arrangement: Five petals; two upper and two lateral petals fused at base to form an upright lobed and arched upper or banner lip; lower petal modified into a large lower lip with convex oval protuberance and short nectar spur. Spur length: About 3.5 mm.

Spur diameter: About 1 mm. Spur texture: Smooth, glabrous. Spur color: Close to 160B. Shape: Upper and lateral petals: Obovate. Lower petal: Roughly rectangular. Apex, all petals: Broadly acute to rounded. Margin: Upper and lateral petals: Entire. Lower petal: Emarginate. Length: Upper petals: About 8 mm. Lateral petals: About 8 mm. Lower petal: About 1 cm. Width: Upper petals: About 6 mm. Lateral petals: About 6 mm. Lower petal: About 1.6 cm. Texture and luster, all petals, upper surface: Smooth, glabrous; velvety. Texture and luster, all petals, lower surface: Smooth, glabrous; matte. Color: When opening, all petals, upper surface: Close to 168A to 168B. When opening, all petals, lower surface: Close to 185B, 185C and 185D. Fully opened, upper and lateral petals, upper surface: Close to 23A; towards the base, close to 34A to 34B; thin streaks at base, close to 187B. Fully opened, lower petal, upper surface: Close to N163C tinted with close to 34B. Fully opened, upper and lateral petals, lower surface: Close to 185D; towards the margins, mottled with close to 185B. Fully opened, lower petal, lower surface: Close to 159A. Throat: Close to 15A.

*Sepals.*—Arrangement: Calyx star-shaped with five sepals fused at the base. Length: About 4 mm. Width: About 1.5 mm. Shape: Lanceolate. Apex: Acute. Margin: Entire. Texture, upper and lower surfaces: Pubescent; minute. Color, upper surface: Close to 146A. Color, lower surface: Close to 146A to 146B.

*Peduncles.*—Length: About 2.5 cm to 3.5 cm. Diameter: About 2 mm. Angle: Terminal racemes are erect and axillary racemes are about 30° to 45° from vertical. Strength: Strong. Texture: Sparsely pubescent. Color: Close to 137B.

*Pedicels.*—Length: About 1 cm. Diameter: About 1 mm. Angle: About 45° from peduncle axis. Strength: Strong. Texture: Sparsely pubescent. Color: Close to 137B.

*Reproductive organs.*—Stamens: Quantity: Four per flower. Filament length: About 1.5 mm. Filament color: Close to 145D. Anther shape: Nearly round. Anther length: Less than 1 mm. Anther color: Close to 6C. Pollen amount: Scarce. Pollen color: Close to 6C. Pistils: Quantity: One per flower. Pistil length: About 2 mm. Style length: Less than 1 mm. Style color: Close to 144D. Stigma shape: Round. Stigma color: Close to 144D. Ovary color: Close to 144C.

*Seeds and fruits.*—Flowers of plants of the new *Nemesia* are sterile and seed and fruit development have not been observed on plants of the new *Nemesia.*

Pathogen & pest resistance: Plants of the new *Nemesia* have not been observed to be resistant to pests and pathogens common to *Nemesia* plants.

Garden performance: Plants of the new *Nemesia* have been observed to have good summer garden performance and to tolerate wind and rain and temperatures ranging from about 5° C. to about 30° C.

It is claimed:

1. A new and distinct *Nemesia* plant named 'Innemblora' as illustrated and described.

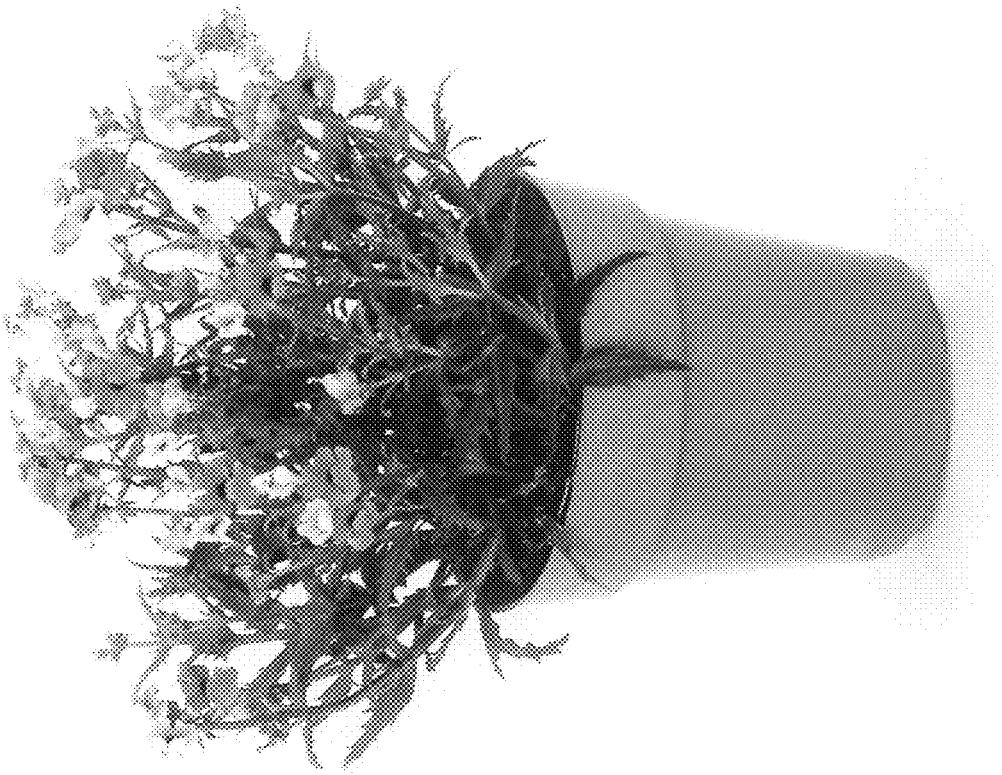
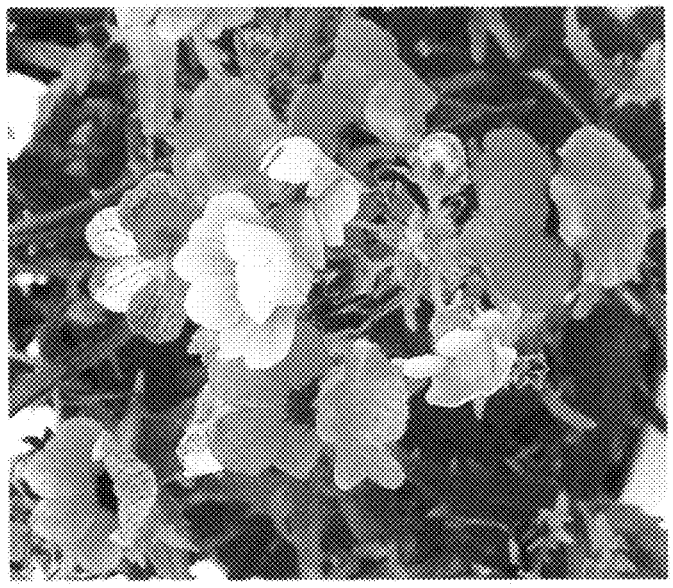

* * * * *